United States Patent
Chapman et al.

(10) Patent No.: US 9,440,243 B2
(45) Date of Patent: Sep. 13, 2016

(54) APPARATUS FOR CENTRIFUGATION AND METHODS THEREFORE

(71) Applicant: MicroAire Surgical Instruments, LLC, Charlottesville, VA (US)

(72) Inventors: John R. Chapman, Sacramento, CA (US); Rodney Sparks, Roseville, CA (US)

(73) Assignee: MicroAire Surgical Instruments, LLC, Charlottesville, VA (US)

( * ) Notice: Subject to any disclaimer, the term of this patent is extended or adjusted under 35 U.S.C. 154(b) by 623 days.

(21) Appl. No.: 13/768,234

(22) Filed: Feb. 15, 2013

(65) Prior Publication Data

US 2013/0210600 A1    Aug. 15, 2013

Related U.S. Application Data

(60) Provisional application No. 61/599,409, filed on Feb. 15, 2012, provisional application No. 61/606,618, filed on Mar. 5, 2012.

(51) Int. Cl.
| | |
|---|---|
| *B04B 7/08* | (2006.01) |
| *B04B 5/04* | (2006.01) |
| *G01N 33/49* | (2006.01) |
| *A61M 1/36* | (2006.01) |
| *A61M 1/02* | (2006.01) |

(52) U.S. Cl.
CPC ............... *B04B 7/08* (2013.01); *A61M 1/029* (2013.01); *A61M 1/3693* (2013.01); *B04B 5/0421* (2013.01); *B04B 5/0442* (2013.01); *G01N 33/491* (2013.01); *A61M 2202/08* (2013.01)

(58) Field of Classification Search
CPC    G01N 33/491; A61M 1/029; A61M 1/3693; A61M 2202/08; B04B 5/04; B04B 5/0421; B04B 5/0442; B04B 7/08
See application file for complete search history.

(56) References Cited

U.S. PATENT DOCUMENTS

| | | | |
|---|---|---|---|
| 4,332,351 A * | 6/1982 | Kellogg | ............... B04B 5/0442 494/10 |
| 6,251,291 B1 | 6/2001 | Lamphere et al. | |
| 6,398,972 B1 | 6/2002 | Blasetti et al. | |
| 6,544,162 B1 * | 4/2003 | Van Wie | ............. A61M 1/3693 494/35 |
| 7,976,796 B1 | 7/2011 | Smith et al. | |
| 9,095,798 B2 | 8/2015 | Chapman et al. | |
| 9,101,925 B2 | 8/2015 | Chapman et al. | |

(Continued)

FOREIGN PATENT DOCUMENTS

| | | |
|---|---|---|
| DE | 19543088 C1 | 3/1997 |
| JP | S49-64864 U | 6/1974 |

(Continued)

*Primary Examiner* — Timothy Cleveland
(74) *Attorney, Agent, or Firm* — Bret E. Field; Khin Chin; Bozicevic, Field & Francis LLP

(57) ABSTRACT

A centrifuge vessel is configured to have at least two chambers therein separated by a divider, and with a spillway around a lip at an end of the divider to join the chambers. After centrifugation differing density phases of an original sample remain on opposite sides of the divider. Separate extraction ports are provided for removal of differing density phases of the original sample from opposite sides of the divider. A method of use of the centrifuge vessel includes centrifugation and extraction at differing orientations of the vessel for convenient and reliable extraction of differing density fractions from the original sample.

7 Claims, 6 Drawing Sheets

(56) References Cited

U.S. PATENT DOCUMENTS

| | | |
|---|---|---|
| 9,101,926 B2 | 8/2015 | Chapman et al. |
| 2005/0123456 A1 | 6/2005 | Eichacker |
| 2005/0247715 A1* | 11/2005 | Ellsworth ........... A61M 1/3693 220/501 |
| 2008/0171645 A1* | 7/2008 | Borgstrom ............... B04B 1/08 494/2 |
| 2011/0021332 A1 | 1/2011 | Akatsu et al. |
| 2011/0143905 A1 | 6/2011 | Kolenbrander et al. |
| 2013/0072903 A1 | 3/2013 | Chapman |

FOREIGN PATENT DOCUMENTS

| | | |
|---|---|---|
| JP | H9-103707 A | 4/1997 |
| JP | 2005-279507 A | 10/2005 |
| JP | 2010-527912 A | 8/2010 |
| RU | 2164172 C1 | 3/2001 |
| RU | 2179893 C2 | 2/2002 |
| SU | 644545 A1 | 1/1979 |
| SU | 948459 A2 | 8/1982 |
| WO | WO2012026970 A2 | 3/2012 |

* cited by examiner

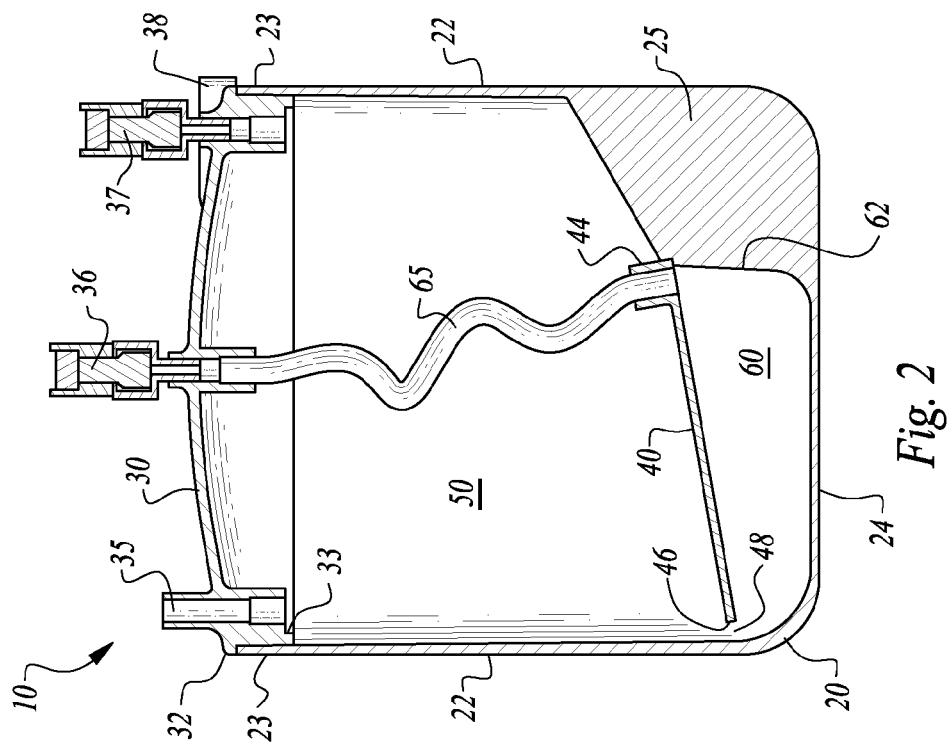
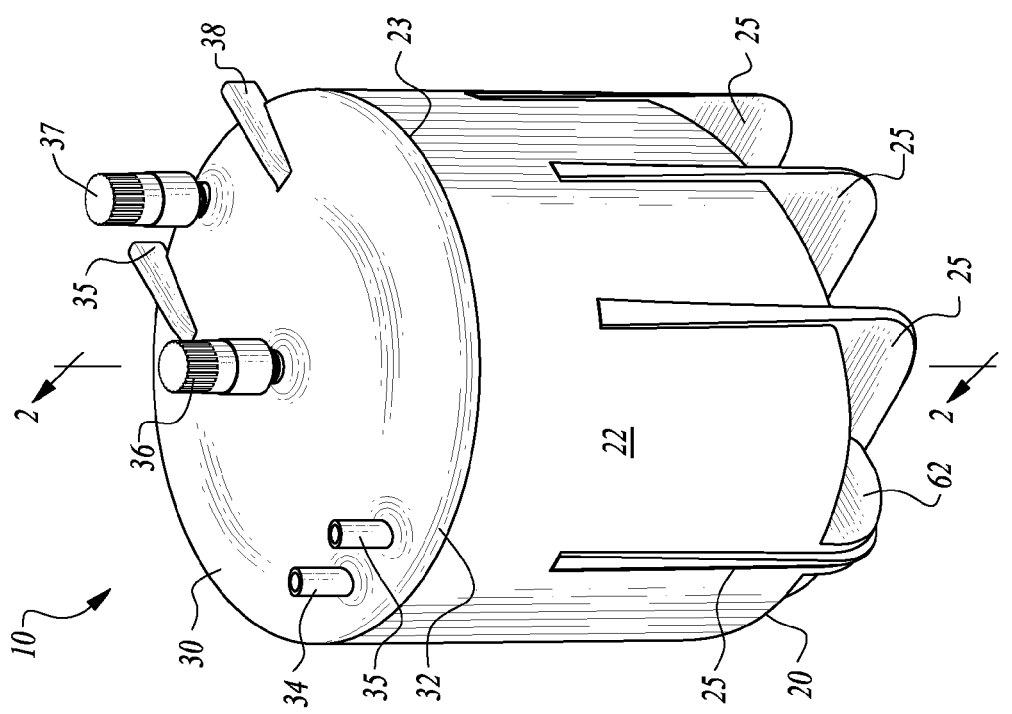
Fig. 2
Fig. 1

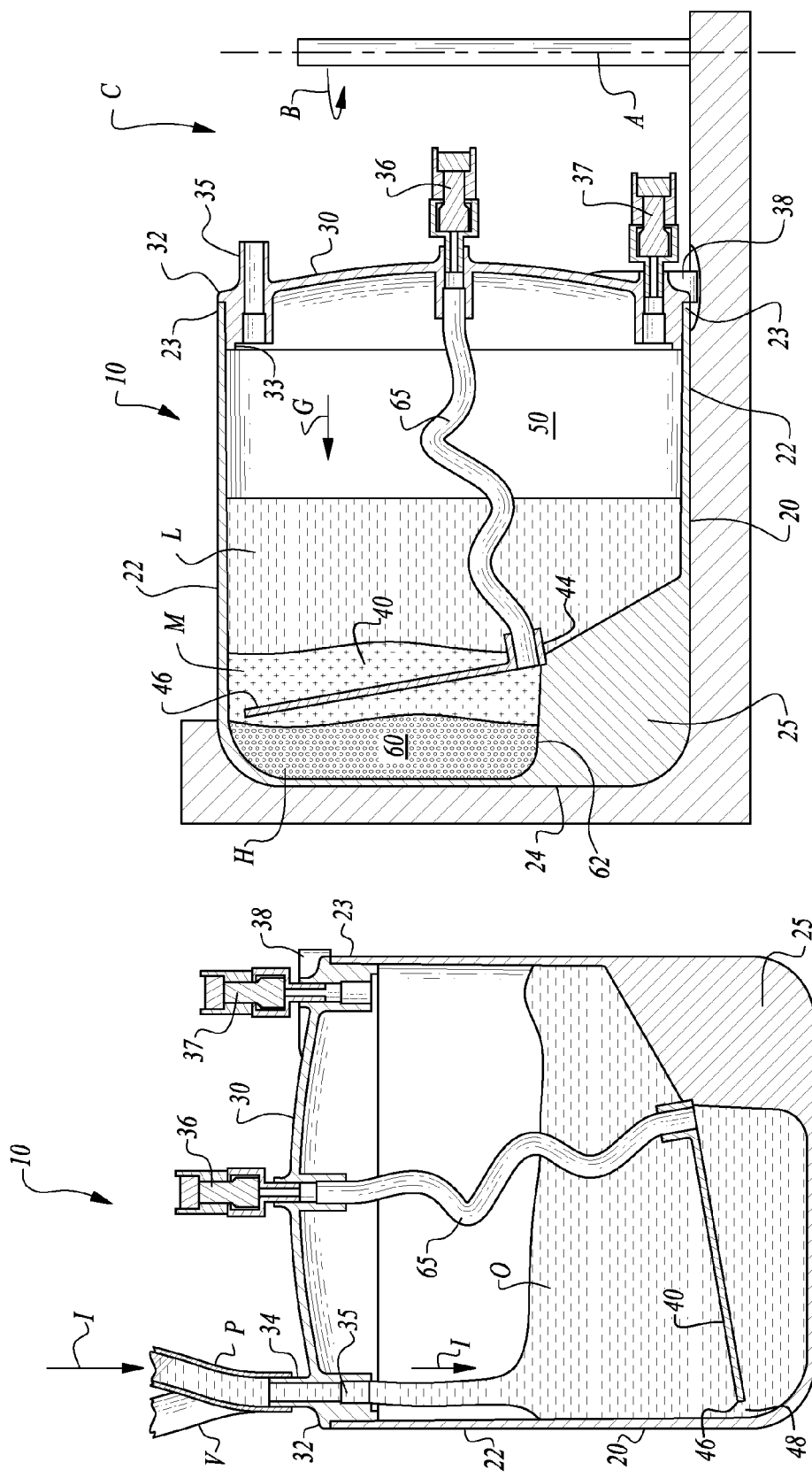

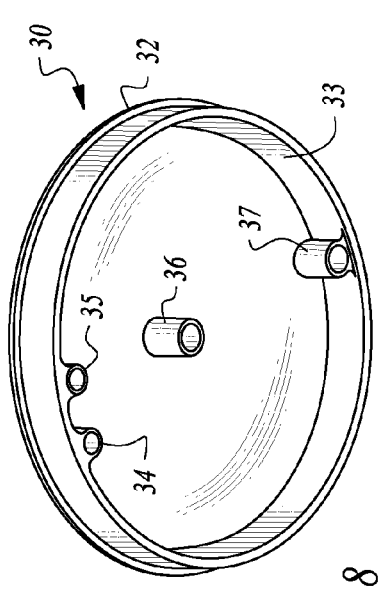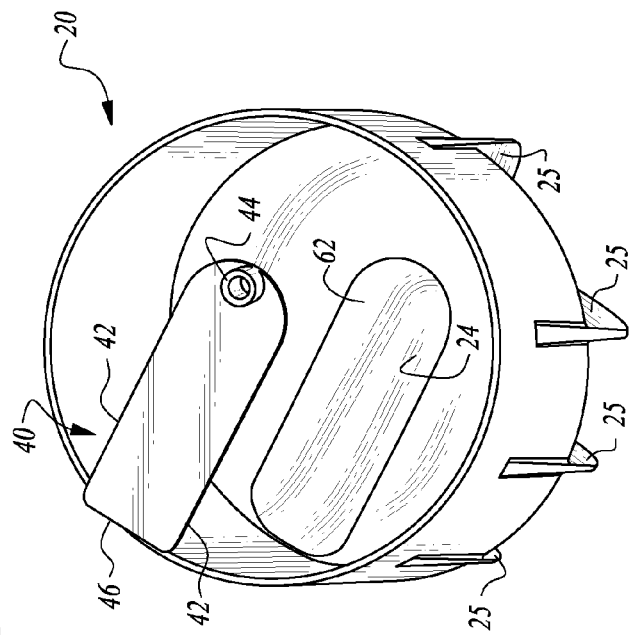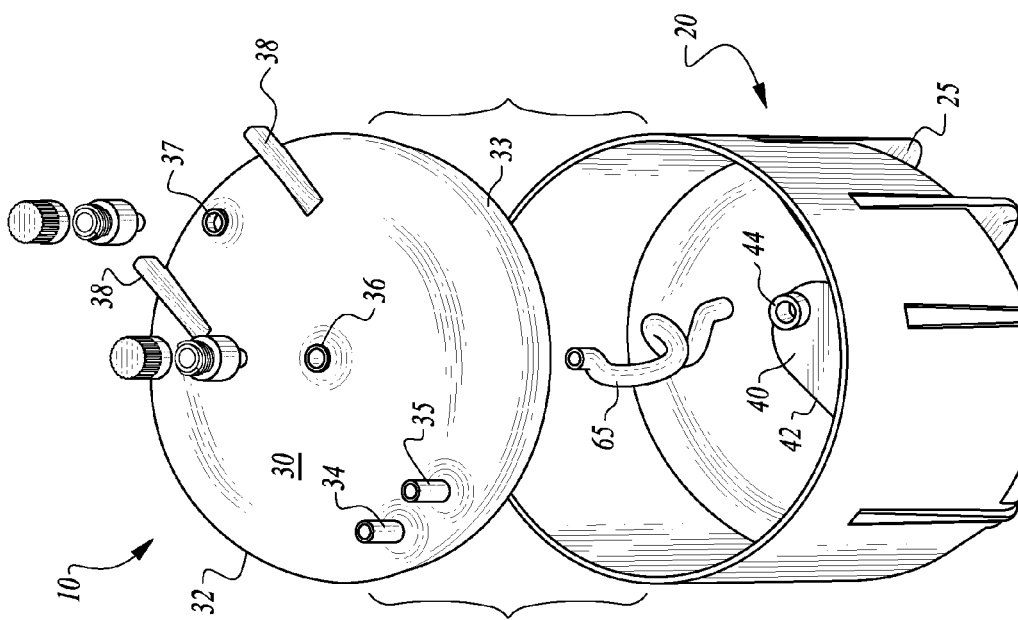

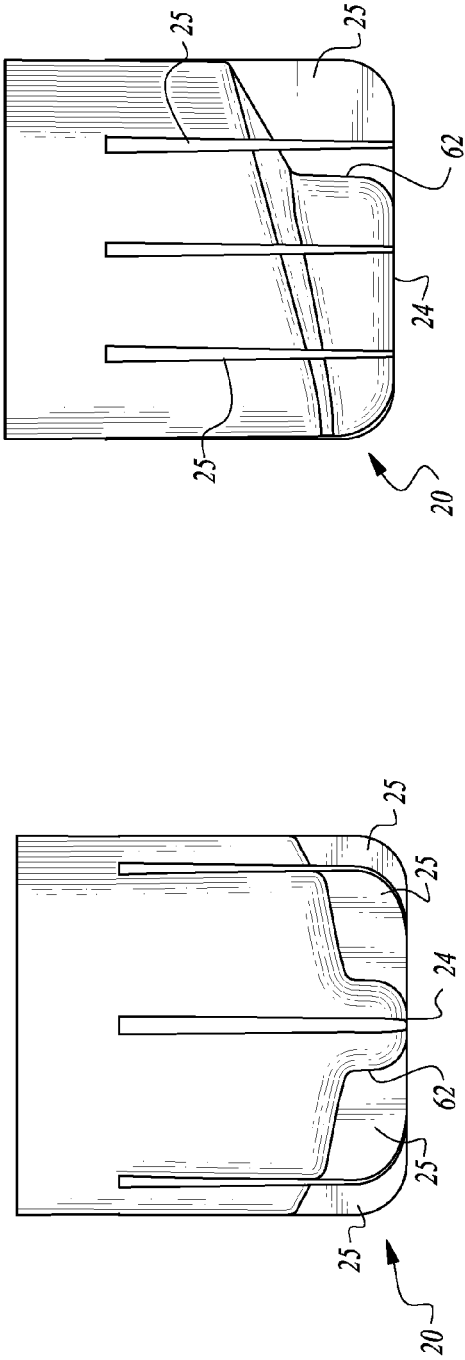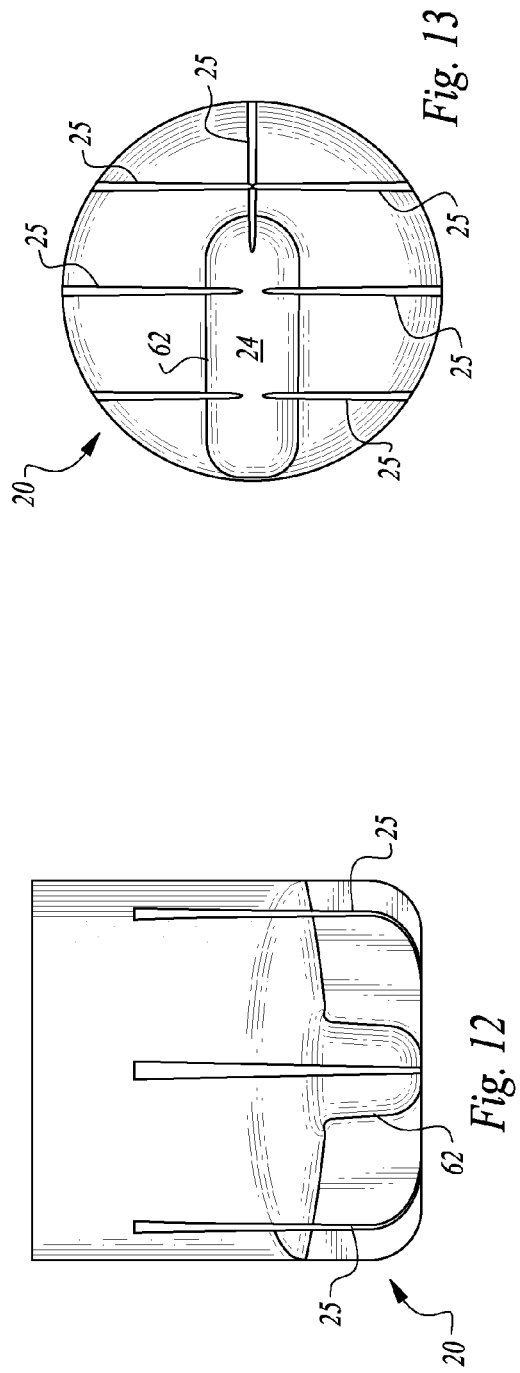

APPARATUS FOR CENTRIFUGATION AND METHODS THEREFORE

CROSS-REFERENCE TO RELATED APPLICATIONS

This application claims benefit under Title 35, United States Code §119(e) of U.S. Provisional Patent Application No. 61/599,409 filed on Feb. 15, 2012 and U.S. Provisional Application No. 61/606,618 filed on Mar. 5, 2012.

FIELD OF THE INVENTION

This invention relates to apparatus and methods for the separation, concentration, collection and washing of density distinguishable constituents contained in a suspending fluid. The invention particularly relates to centrifuges, vessels and centrifuge operation methods which utilize sample containing vessel geometry to maintain separation of density phase layers after centrifugation and during harvest of density fractions. In some embodiments, the invention discloses a means to utilize or separately extract a medium density fluid to further facilitate separating the differing density fractions contained in a mother fluid.

BACKGROUND OF THE INVENTION

Essentially a centrifuge is an apparatus that separates differing density constituents that are in a fluid. Centrifugation provides a means for achieving two goals through one approach: differing density constituents can be both concentrated and purified under centrifugal forces. Centrifugation causes the heavier particles or constituents to sediment rapidly in the direction outward from the center of rotation. The centrifugal force generated by centrifugation is proportional to the speed of rotation and the radius of the rotor. Gee force is the force acting on a body as a result of acceleration or gravity. At a fixed centrifugal force and medium viscosity, the sedimentation rate of the particle is proportional to the molecular weight of the particle and the difference between its density and the density of the medium. This observation has led to the use red cell aggregating agents such as HESPAN™ (hydroxyl-ethyl starch) to enhance the differential stratification of red cells from leukocytes by centrifugation. The use of this type of sedimentation agent is applicable to the present invention.

The principles of centrifugation for cell separation have been reviewed in a U.S. patent application of Chapman and Sparks entitled "Centrifuge and Separation Vessel Therefore" having application Ser. No. 13/199,111 and published as Publication No. 2012/0065047 on Mar. 12, 2012, the entire contents of which are incorporated herein by reference.

Centrifuges are suited and used for the separation of components including cells, organelles or macromolecules contained in biologic fluids including bone marrow, peripheral blood, urine, phlegm, synovial semen, milk, saliva, mucus, sputum, exudates, cerebrospinal fluid, amniotic fluid, cord blood, intestinal fluid, cell suspensions, tissue digests, tumor cell containing cell suspensions, microbe containing cell suspensions, radio-labeled cell suspensions and cell culture fluid for therapeutic or diagnostic purposes.

Centrifuges are well suited for the washing of cell suspensions and other particulate matter. Centrifuges also are used for separation of components present in aqueous solutions, lake water, ocean water, river water, waste water, and sewage for the purpose of preparative analytical testing or purification. Centrifuges are also suited for the separation of a component of an inorganic or organic chemical reaction that has resulted in the formation of a precipitate or flocculent. Centrifuges are employed in industrial applications including manufacturing and purification in food and beverages, in metallurgy, mining of precious metals including gold, silver and platinum. Centrifuges have been used for separation of particulates added to an aqueous solution for the purpose of inducing a chemical reaction and then terminating said chemical reaction by centrifugation of the heterogeneous fluid using the apparatus of the invention. Centrifuges have been used to in combination with density particles to perform immunoaffinity cell separation steps which is also applicable to the present invention. This expansive list is still not inclusive for all the varied functions for which centrifuges are routinely employed and are applicable to the present invention. Detailed examples of centrifuge vessels employed in these applications are summarized in U.S. Provisional Application No. 61/401,877 filed on Aug. 21, 2010, the entire contents of which are hereby incorporated herein by reference.

The present invention in some of its embodiments also relates to the field of medical suction canisters and more particularly to a suction canister assembly designed for the safe collection, centrifugal separation of body fluids from a patient, harvesting of one or more fractions of the separated lipoaspirate for use in therapeutic or cosmetic applications.

During the course of a surgical operation on a patient, it is often necessary to remove from the site of the operation various body fluids including blood, tissue fragments, and other viscid fluids which tend to collect at the operation site. Removal of such body fluids is generally accomplished using an aspirator connected to a source of vacuum to draw the fluids through a suitable tube for deposit into a collection bottle or canister. Body fluid storage canisters for use in such systems are well known in the art. Typically, such canister assemblies include a canister and cover which are secured together with a leak tight seal. Two connections are provided in the cover, a vacuum port for being connected by a tube or other suitable connections to a source of vacuum, for example, a vacuum pump or hospital vacuum outlet station. The other connection comprises a fluid receiving port which is connected through a drainage tube to the surgical operating site on a patient. In the suction canister, a vacuum is produced to create a vacuum in the tube leading to the operation site from which fluids are to be withdrawn. This vacuum carries the fluid through the drainage tube to an inlet in the suction canister enabling complete or partial filling of the canister.

Vacuum aspiration has become popular in several surgical procedures including fat liposuctions. Among the most common liposuctions are typically accomplished by inserting the distal end of a narrow metal cannula through a small incision in the skin and applying a vacuum suction, generally through a hose attached to the proximal end of the cannula. Liposuction cannulas generally consist of a hollow handle in which the shaft of the cannula is inserted. Various tip and hole configurations through which fat is suctioned are situated at the distal end of the cannula. After inserting the distal end of the cannula through the incision in the skin, the surgeon carefully moves the cannula forward and backward within the layer of fat. This movement shears off fat tissue particles, which are drawn into the cannula and out of the body by the vacuum. The hose leads to a suction canister, which is designed to hold the adipose tissue and its fluid constituents.

In U.S. Pat. No. 5,786,207 to Katz et al., issued Jul. 28, 1998, the entire contents of which are incorporated herein by reference, discloses a device for dissociating tissue into a single cell suspension. The problems identified by Katz and Lull for processing lipoaspirate included the viscosity of the tissue sample being further increased by the oil released from cells damaged during the liposuction procedure or cell separation process. They also noted lipoaspirate having a thick, slurry-like consistency which is caused by oil, serum, tissue fragments and other fluids. They further noted the consistency of such liposuctioned tissue, particularly large samples of such tissue, causes occlusion of filtering mechanisms and is a significant hindrance to thorough, effective washing and cell separation.

Suction canisters are known for floor, cabinet and wall mounting, generally for medical uses to provide suction at a patient bedside for various purposes such as wound cleansing, sanitation purposes, aspiration and the like. The canister includes a plastic or glass container which can be of different sizes onto which a plastic lid is fitted. The lid is formed with tubular fittings or ports connectable to a suction inlet hose and a patient outlet hose.

Said suction canister are known in the prior art to be hard suction canister wherein the walls of the vessel are sufficiently strong to within stand implosion as a result of the vacuum force applied and also to be construction of single use disposable suction canister liners which are housed in reusable hard canister to provide support for the suction canister during the lipoaspiration procedure.

It is known in the prior art to have lids of hard suction canister or lids of suction canister liners to include a one-way valve built into the inner lid at the patient port to prevent back flow of fluid into the tubing connected to the cannula.

An automatic shutoff valve is known in the prior art to be located inside the lid of a hard suction canister or the lid of a suction canister liner to help prevent cross contamination of regulators and wall vacuum outlets. In addition, 90° adapters allow tubing to connect at right angles to help prevent kinking and impeded fluid flow. The use of locking lids has been reported to encourage the proper disposal of infectious liquid medical waste and enhances worker safety. Lid includes accessory and orthopedic ports. The volume of the canister is typically in the range of 100 ml to 3 liters.

The present invention in some of its embodiments relates to cell salvage where cells removed from the body during a surgical procedure are subsequently returned to the body. Prior art systems for salvaging blood from surgical sites and wound drains often employ disposable units that include a reservoir for collecting the blood-containing fluid and a separation device (such as a centrifuge bowl or disk) for separating out and washing the red blood cells (RBCs). The RBCs salvaged using these systems may be auto-transfused back into the patient, thereby reducing the need for allogenic blood transfusions. Examples of such blood-salvage systems include those described in U.S. Pat. No. 6,251,291 to Lamphere et al., issued Jun. 26, 2001, and in U.S. Patent Application Publication No. 2005/0203469 by Bobroff et al., published Sep. 15, 2005 and U.S. Patent Application Publication No. 2008/0108931 by Bobroff published May 8, 2008. Both this patent and published applications are incorporated herein by reference. Blood and other fluids are suctioned from a surgical site and drawn into the reservoir. These fluids are drawn from a reservoir into a centrifuge, which is then spun so as to separate out the red blood cells from the plasma and other fluids. The plasma and other fluids may be directed to a waste bag. The red blood cells may then be washed in the centrifuge disk with saline from the saline source. After washing, the saline may be separated from the RBCs and directed to the waste bag, and the washed red blood cells directed to the red blood cell bag. The red blood cells may then be retransfused into the patient. Often the amount of blood collected in the reservoir is insufficient to carry out the separation and wash procedures. In such a situation, the entire disposable set must be discarded after the procedure. This is wasteful and adds unnecessary expense to surgical procedures that ultimately do not lead to washing and reinfusing of blood to the patient.

The present invention in some of its embodiments relates to the field of cell washing. A particularly important clinical problem is the lack of an effective means to wash away toxic cryopreservative agents present in thawed cell suspensions. DMSO is such a toxic solvent commonly used for the cryopreservation of autologous peripheral blood stem cells, cord blood, and bone marrow. Infusion reactions are expected to occur and include nausea, vomiting, fever, rigors or chills, flushing, dyspnea, hypoxemia, chest tightness, hypertension, tachycardia, bradycardia, dysgeusia, hematuria, and mild headache. Severe reactions, including respiratory distress, severe bronchospasm, severe bradycardia with heart block or other arrhythmias, cardiac arrest, hypotension, hemolysis, elevated liver enzymes, renal compromise, encephalopathy, loss of consciousness, and seizure also may occur. The frequency and severity of these adverse reactions are related to the amount of DMSO administered. Minimizing the amount of DMSO administered may reduce the risk of such reactions, although idiosyncratic responses may occur even at DMSO doses thought to be tolerated. The actual amount of DMSO depends on the method of preparation of the product for infusion. A method for the efficient washing of thawed cryopreserved cells concentrates is therefore a significant unmet need. Other unmet needs for cell washing include removal of enzymes such as collagenase from tissue digests, removal of density media such as Ficoll following density phase separation and removal of lytic reagents after selective cell lysis. It is particularly desirable to have a cell washing system that can be scaled and is simple enough to be used at the point of care when dealing with medical applications.

None of the devices disclosed above adequately address the special processing concerns presented for concentrating viable cells from tissues for medical and veterinary therapeutic applications, diagnostic applications, cosmetic applications wherein simplicity, speed and reliability are highly valued. The ability to conduct cell concentrating, washing, and purification of heterogeneous biological fluids at the intra-operative point of care is particularly important for regenerative medicine and cosmetic surgery applications. Although various vessels for concentrating, washing and purifying biological fluids are documented in the literature, a need exists for a device and method that is more expeditious, efficacious, accessible and practical than current devices and methods. Further, devices do not currently exist that have successfully addressed the technical challenges and operator needs in processing lipoaspirate where the range of volume is high (20 ml to 3 liters) and the fluid is particulate in nature. Therefore, a long held need has existed for a device and method that can enable an operator without special skill and training to prepare volume reduced viable cell concentrates from biological fluids in a practical and reliable manner. What is needed is a single device that enables both the collection of the lipoaspirate and its separation by centrifugation into phase components based upon density and the means to extract one or more of these density phases for use in therapeutic or cosmetic procedures in a simple and reliable manner.

SUMMARY OF THE INVENTION

With this invention, a vessel is provided for use in a centrifuge which utilizes unique geometry to stratify a heterogeneous multi-constituent fluid sample into fractions of different densities and to physically separate such fractions after centrifugation.

The invention can be applied to achieve volume reduction, concentration, and purification of heterogeneous fluids based upon differences in density of the fluid components.

The fluid processed with the present invention can be biologic or non-biologic in origin. The vessel is in the form of a housing which includes an interior space contained within an outer wall including a side wall extending up from a floor. A barrier divides this interior space of the vessel into at least two regions or chambers. These two regions are joined together over a top of a lip of the barrier defining a lowermost most portion of the barrier (i.e. closest to the floor), so that the two regions come together on a lower portion of the vessel, but are spaced from each other by the barrier otherwise.

The vessel housing has a higher gee floor and a lower gee lid, respectively defined by the portion of the vessel most distant from a spin axis of the centrifuge and closest to the spin axis of the centrifuge, when the vessel is positioned within a cradle or other vessel support of the centrifuge. The barrier is oriented to divide the interior space of the vessel into the higher gee lower chamber and the lower gee upper chamber. Thus, after centrifugation is complete, and spinning of the centrifuge stops, higher density fractions remain on a higher gee lower side of the barrier with lower density fractions remain on the lower gee upper side of the barrier.

Furthermore, sample separation can be accelerated by providing a face of the barrier closest to the spin axis with a taper. This taper is selected so that portions of the face closest to the lip are most distant from the spin axis with portions of the face most distant from the lip closest to the spin axis. This taper can be flat or curving, such as a concave curve, with different contours on the face adjusting the separation rate.

The vessel benefits from being configured for the specific sample to be separated. In particular, the lip of the barrier can be positioned and/or the region volumes selected to match expected percentage constituents of each fraction within the sample. This correlation can be exact or merely general in nature. With such vessel optimization, the barrier maintains separation of the fractions from each other after the centrifuge stops spinning for easier and more complete measurement, collection or other post separation processing.

In one embodiment, the centrifuge is configured so that the vessel is oriented upright during centrifugation. In such an embodiment the barrier could be vertical with the face and side opposite the face also being vertical. Preferably, the face tapers so that the barrier has a greater width spaced from the lip than at the lip. This taper can be flat or concave. The vessel can be configured with inlet and outlet tubes which access regions on opposite sides of the barrier. These tubes are utilized for introduction of the sample into the vessel and for removal of higher and lower density fractions from the vessel after centrifugation.

In a second embodiment, the centrifuge is configured to support the vessel at an angle away from vertical at least somewhat with upper portions of the vessel closer to the spin axis than lower portions of the vessel. In such a centrifuge, the barrier has a face which is tapered at an angle which causes the tip of the barrier to be further from the spin axis than portions of the face spaced from the tip. With such a configuration, higher density fractions of the sample can over time migrate down the face of the barrier, over the lip and into the catch basin. Similarly, lower density fractions which might begin within the higher density region of the centrifuge can migrate up over the lip of the barrier and into the lower density region of the centrifuge.

For certain separations where higher density fractions are present in relatively small overall percentages of the sample, the higher density region on the higher density side of the barrier benefits from being configured to have a small volume similar to but slightly more than an expected percentage for the higher density fraction of the sample. In this way, a relatively small higher density fraction fills a majority or at least a relatively large minority of the higher density region of the vessel. The higher density fractions of the specimen can then be relatively easily distinguished from the higher density region after spinning of the centrifuge has ceased. The vessel can be configured with inlet and outlet tubes which access regions on opposite sides of the barrier. These tubes are utilized for introduction of the sample into the vessel and for removal of higher and lower density fractions from the vessel after centrifugation.

In one embodiment, the vessel is removed from the centrifuge carrier and configured so that the vessel is oriented to rest on a side wall such that the lip is in the uppermost position. In this position, a complete physical separation can occur between the fluids in the upper and lower chambers, provided the vessel contains sufficient air to occupy the space between the lip and the proximate side wall. Using the inlet and outlet tubes, fluids can be removed or added from or to either the upper or lower chamber without intermingling of the higher and lower density fractions.

In another embodiment, separation of the differing density fractions of the sample is facilitated by including a medium density fluid within the interior space of the vessel or other enclosure. This medium density fluid has a density selected to be intermediate between the densities of the at least two constituents to be separated. After centrifugation, the medium density fluid is interposed between the higher and lower density constituents to increase a spacing between the higher and lower density constituents. By further selecting the medium density fluid to be a non-contaminating substance that can be collected with the other constituents without negative consequences, nearly complete collection of one (or both) of the differing density constituents can be achieved without contaminating the collected constituent with any portion of the other constituent therein.

In this embodiment a centrifuge vessel is provided with an optimized geometry for separation with such a medium density fluid. In particular, the barrier within the vessel separates a reservoir on a lower gee side of the barrier from a catch basin on a higher gee side of the reservoir. Higher density constituents collect within the lower end of the catch basin for separate removal. The vessel is removed from the centrifuge carrier and strategically positioned such that the vessel is oriented to lie horizontally on its side, such that the lip is in the uppermost distant position possible from the opposite side contacting the supporting surface. In this horizontal position, a complete physical separation occurs between the fluids in the upper and lower chambers. Using the inlet and outlet tubes connected to the chambers, fluids can be removed or added from or to either the upper or lower chamber without intermingling of the higher and lower density fractions.

OBJECTS OF THE INVENTION

Accordingly, a primary object of the present invention is to provide a vessel for use in a centrifuge which keeps differing density fractions of a sample separate after centrifugation.

Another object of the present invention is to provide a centrifugation vessel which facilitates more rapid separation of differing density fractions therein.

Another object of the present invention is to provide a centrifugation vessel which collects at least some differing density fractions of a sample within a defined space to be more readily measured, removed or otherwise analyzed or processed.

Another object of the present invention is to provide a centrifugation vessel which is customized for the separation of a particular sample into expected fractions.

Another object of the present invention is to provide a centrifugation vessel optimized for separation of a biological sample into at least two fractions of differing densities.

Another object of the present invention is to provide a method for separation of a sample into differing density fractions which also keeps the differing density fractions separate after separation.

Another object of the present invention is to provide a method for separating and collecting a fraction of a sample after centrifugation.

Another object of the present invention is to provide a centrifuge which separates and collects fractions of different densities from a sample.

Another object of the present invention is to provide a method and apparatus for separating particulate containing fluids into at least two differing density fractions without the need for any moving parts, to enhance operational reliability.

Another object of the present invention is to provide a separating method for separating a higher density constituent of a sample from at least one other portion of the sample by centrifugation along with a medium density fluid having a density between the density of the higher density constituent and the density of the at least one other portion of the sample.

Another object of the present invention is to provide a method for separation of a portion of a target cell population within a first solution from soluble contaminates within the sample while avoiding co-mingling of the separated constituents during a removal procedure, and in a manner which can be performed quickly and reliably.

Another object of the present invention is to provide a separation method which utilizes a centrifugation vessel which is at least partially transparent so that an operator can visually monitor the success of the separation.

Another object of the present invention is to provide a centrifuge vessel that can be used to reduce the presence of undesired contaminants from a cell suspension.

Another object of the present invention is to provide a multi-purpose vessel that can act as a suction canister for harvesting of biological fluids from a body and as a centrifuge vessel to prepare density fractions from harvested biological fluid for a therapeutic, a diagnostic, a graft additive, a cosmetic or a research application.

The current invention solves many problems in cell separation by integrating the functions of being a suction canister and a centrifugation canister with density phase separation capability. A notable advantage of the present invention is the ability of the centrifuge canister to physically separate into two discrete non-contacting samples comprising a low density and a high density fraction. This complete separation enables mixing and harvest of the sample fractions without risk of intermingling of the density fluid layers.

Because of the heterogeneous nature of biological fluids, it is frequently difficult to transfer them from one container to another without causing unintended loss of material and increasing processing time. Further such fluid transfer can compromise the safety of the sample by introducing the risk of microbial contamination. Further, the amount of medical waste and related costs can be reduced by integrating different functions into a single device.

One object of the present invention is that the centrifuge vessel can be used as a suction canister for the harvest of biological fluids including blood, blood fractions, lipoaspirate, lipoaspirate fractions, bone marrow, and tissue fragments and combinations thereof. After centrifugal separation of the biological fluid, the centrifuge vessel geometry design enables a high and a low density fraction of the biological fluid to be harvested. By creating a centrifuge vessel integrating the functions of harvesting lipoaspirate by vacuum aspiration directly from the cannula used to probe the patient with the capability to centrifuge the same container and further designing a means for removal of a cell fraction formed by centrifugation, the present invention enables the quick and efficient preparation of lipoaspirate derived cellular compositions for therapeutic and cosmetic clinical applications at the point of care.

The dual use canister assembly consists of material composition to achieve a rigid container or to be a rigid container with a non-rigid container lining chamber for processing lipoaspirate. An example of a suitable rigid container material is polycarbonate. An example of a suitable non-rigid container inner lining material is polyvinyl chloride (PVC). The design and composition of the rigid container is such to withstand the implosive forces when its inner chamber has an air pressure less than atmospheric pressure so as to enable the collection of the lipoaspirate during lipoplasty. Further the design and composition of the rigid container is such that it will fit into a centrifuge bucket and withstand forces of centrifugation of at least 100×g for at least 5 minutes. Preferably, the canister can withstand forces of at least 2,000×g for 30 minutes. In the disclosed invention the canister is centrifuged for a sufficient period at a sufficient g-force to cause stratification of the lipoaspirate components into different fluid phase layers based upon differences in density of the fluid components. Further the design of the rigid container or the liner container supported by the rigid container enable the harvesting of one or more density phase layer formed during centrifugation. The said collected fraction is used for a therapeutic or cosmetic purpose.

In another embodiment, the suction canister is supplemented with an anticoagulant to prevent the formation of fibrin, which can potentially interfere with the harvesting step of the cellular components.

While the invention has been described, the same is to be considered as illustrative and not restrictive in character, it being understood that only the preferred embodiment has been shown and described and that all changes and modifications that come within the spirit of the invention are desired to be protected.

One advantage of the present invention in one or more of its embodiments is to reduce the problem of needing to transfer the tissue fragments from once vessel to another during the process. Another advantage of the present invention in one or more its present embodiments is to increase the number of cells that can collected from tissue fragments. This is important because in general biological experience has shown that more cells have greater therapeutic potential than fewer cells. Another advantage of the present invention in one or more its present embodiments is to reduce the total processing time to have a useful cell suspension derived from tissue fragments. This time savings can enable the invention to be performed in the intra-operative theatre instead of a laboratory setting which greatly reduces cost associated with the tissue processing. Intra-operative processing of tissues also ensures improved safety as there is no risk of tissue samples being mixed up and the cells inadvertently being administered to the wrong patient.

The vessel is preferably injected molded using medical grade plastic such as polystyrene, polycarbonate or polypropylene such that it can pass required tests for biocompatibility including toxicology assays for cytoxicity, hemolysis, and sensitization. The vessel is preferably sterilized before use with a human patient sample by gamma irradiation, ethylene oxide, E-beam irradiation or autoclaving so as to have a sterile fluid path. The vessel is preferably manufactured in a manner so as to pass assays for detecting the presence of excessive amounts of pyrogenic substances such as endotoxin.

The principles of centrifugation for cell separation have been reviewed in the U.S. patent application of Chapman and Sparks entitled "Centrifuge and Separation Vessel Therefore" having application Ser. No. 13/199,111 and Publication No. 2012/0065047 published on Mar. 12, 2012, the entire contents of which are incorporated herein by reference. This patent application also describes a centrifuge canister suitable for use in the present invention by modifying the lid of the canister to become a suction canister having a port for the introducing of fluid into the interior of the canister through one port in the lid, and there being a second opening in the lid for the attachment of a vacuum source to provide a means for drawing the fluid into the canister.

In one embodiment, the canister has a sterile and non-pyrogenic fluid contacting interior. Biological safety is also improved by the use of closed system for the vessel used to carry out the design so as to reduce the risk of microbial contamination of the cells prepared with the disclosed method.

In one embodiment, the canister includes a filtration system to prevent the migration of undesired solids during the extraction process. An example of a filtration system is a particulate filter used in intra-venous fluids or a clot filter used in blood transfusions.

The fluid may be biological in origin and contain living cells. Cells contained in the cell composition may include but are not limited to the list comprising stem cells, progenitor cells, mesenchymal stem cells, endothelial progenitor cells, hematopoietic stem cells, dendritic cells, tumor infiltrating lymphocytes, muscle cells, liver cells, spleen cells, lung cells, heart cells, neurons, astrocytes, glial cells, epithelial cells, skin cells, dermis cells, macrophages, fibroblasts, pericytes, adipocytes, and blood cells including leukocytes, red blood cells and platelets.

Examples of useful biological fluids for use with the present invention include but are not limited to cell containing fluids derived from adipose, bone marrow, umbilical cord and placenta.

A particularly useful source of cells and tissue fragments for use with the present invention are derived from adipose in the form of lipoaspirate. The present apparatus and method can readily be scaled to handle the volume of sample generated by liposuction.

Various advantages of this invention will become apparent to those skilled in the art from the following detailed description of the embodiments, when read in light of the accompanying drawings.

Other further objects of the present invention will become apparent from a careful reading of the included drawing figures, the claims and detailed description of the invention.

BRIEF DESCRIPTION OF THE DRAWINGS

FIG. 1 is a perspective view of a centrifuge vessel for use as at least a portion of an apparatus of this invention and to perform methods according to this invention.

FIG. 2 is a full sectional view of the centrifuge vessel of FIG. 1.

FIG. 3 is a full sectional view similar to that which is shown in FIG. 2, but with the vessel shown with a fluid sample being loaded into the vessel.

FIG. 4 is a full sectional view of the vessel of FIGS. 1-3 after it has been loaded into a centrifuge and is in the process of being centrifuged, and showing the sample separating into separate density phases.

FIG. 7 is a perspective exploded parts view of that which is shown in FIG. 1.

FIG. 8 is a perspective view from below of a cover portion of the vessel shown in FIG. 1.

FIG. 9 is an exploded parts view of a housing portion of the centrifuge vessel of FIG. 1.

FIGS. 10-12 are various side elevation views of the housing of FIG. 9.

FIG. 13 is a bottom plan view of the housing of FIG. 9.

DESCRIPTION OF THE PREFERRED EMBODIMENT

Figures 5, 6:
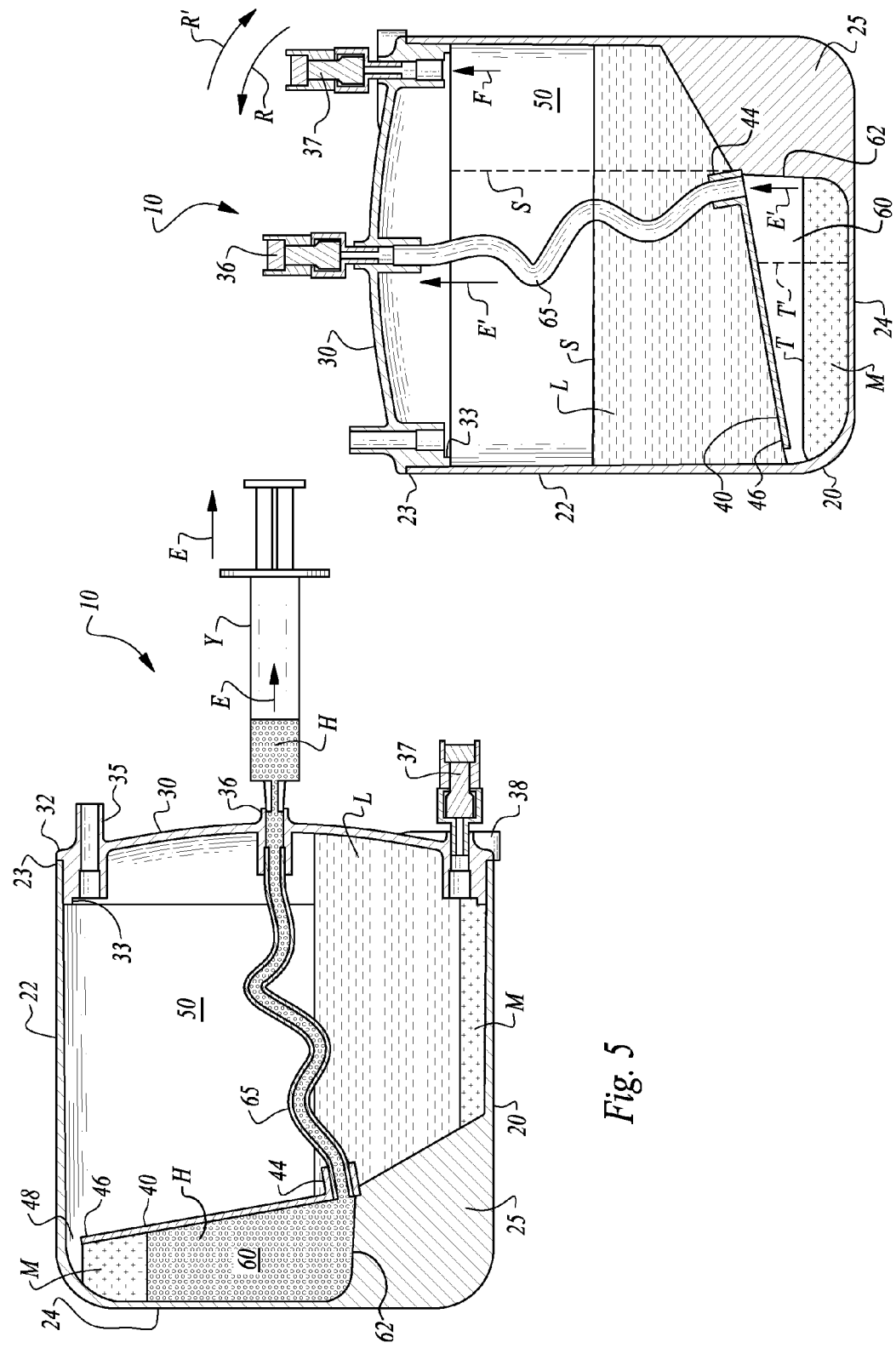
FIG. 5 is a full sectional view similar to that which is shown in FIGS. 1-3, but with the vessel on its side and with a high density phase isolated in a lower chamber and being removed from the lower chamber of the vessel.
FIG. 6 is a full sectional view of that which is shown in FIG. 5 after removal of the high density phase and with various rotations of the vessel depicted for extraction of a medium density phase and a low density phase according to methods of this invention.

Referring to the drawings, wherein like reference numerals represent like parts throughout the various drawing figures, reference numeral 10 is directed to a centrifuge vessel, defining at least a portion of an apparatus according to one embodiment of this invention. The vessel 10 can be used to separate an original mixed density sample O into separate constituents having differing densities. The vessel 10 also is conveniently configured to keep the distinct constituents separate after centrifugation and to provide for convenient removal of separate constituents after centrifugation.

Any multi-constituent fluid sample having constituents of differing densities can be separated within the centrifugation vessel 10, with a specific example provided herein involving the separation of a biological fluid (e.g. lipoaspirate) into a high density phase (such as a cell pellet) from a low density phase (such as adipose tissue and/or other oils) and potentially also a medium density phase (such as an aqueous phase) of a medium density between the density of the high density phase and the density of the low density phase.

In essence, and with particular reference to FIGS. 1, 2 and 7, basic details of the centrifuge vessel 10 are described, according to this preferred embodiment. The vessel 10 is an enclosure generally formed of a housing 20 and a cover 30. The housing 20 has an interior including an upper chamber 50 above a lower chamber 60. A divider 40 separates the upper chamber 50 from the lower chamber 60. The divider 40 allows for flow between the two chambers 50, 60 through a spillway 48 adjacent a lip 46 of the divider 40. An extraction tube 65 is also provided which extends from the lower chamber 60 and through the cover 30, for removal of a high density phase H fluid after centrifugation and without concern for remixing the high density phase H with the medium density phase M or low density phase L fluids within the vessel 10.

The divider 40 beneficially has an angle which causes the lip 46 of the divider 40 to be closer to a floor 24 of the housing 20 than any other portion of the divider 40. In this way, high density phase H fluid avoids becoming trapped within the upper chamber 50 and low density phase L fluid avoids becoming trapped within the lower chamber 60, and separation is accelerated. As depicted in FIG. 5, after centrifugation the centrifuge vessel 10 can be laid on its side and the high density phase H fluid remains trapped within the lower chamber 60 and separated from the low density phase L fluid that remains within the upper chamber 50. The high density phase H fluid can then be conveniently extracted through the extraction tube 65 (along arrow E of FIG. 5) such as by utilization of a syringe Y.

More specifically, and with particular reference to FIGS. 1, 2, 7 and 9-13, particular details of the housing 20 of the centrifugation vessel 10 are described, according to this exemplary embodiment. The housing 20 preferably forms a first part of the centrifuge vessel 10, with the cover 30 providing the second part. The housing 20 is a rigid open topped enclosure which is closed off by the cover 30. This housing 20 thus includes side walls 22 extending up from a floor 24 to a rim 23. Fins 25 preferably extend outward from the floor 24 and to some extent from the side walls 22. These fins 25 add rigidity to the side walls 22 so that the side walls do not need to be as thick as they would otherwise be required to be to withstand the high forces associated with operating within a centrifuge and vacuum within the vessel 10.

The housing 20 is preferably formed of a polymeric hydrocarbon material of a type which exhibits high strength suitable to avoid deformation or other failure when in a high gee load environment, such as that within a centrifuge. Most preferably, the material is suitable for forming by injection molding and the geometry of the side walls 22, floor 24 and fins 25 are selected to allow the housing 20 to be readily formed by injection molding without excessive mold complexity. For instance, while the side walls 22 are preferably substantially cylindrical, they can have a slight draft which causes the side walls 22 at the rim 23 to be slightly greater in diameter than portions of the side walls 22 extending toward the floor 24, such that the housing 20 can easily pop out of a two-piece mold with one piece forming an interior of the housing 20 and one piece of the mold forming an exterior of the housing 20 along with the fins 25. The material is also preferably biocompatible and able to withstand autoclaving and other sterilization techniques. The vessel 10 can be either reusable or single use disposable.

The basic geometry of the housing 20 is that of a cylinder with the side walls 22 being cylindrical about a centerline extending through a substantially circular floor 24. The floor 24 generally defines a lowermost portion of the housing 20 and a portion of the housing 20 configured to be most distant from a spin axis A of a centrifuge C (FIG. 4), so that high gee forces G (FIG. 4) exerted upon the centrifuge vessel 10 are exerted down toward the floor 24 when the centrifuge vessel 10 is in use. However, the floor 24 is not always necessarily below other portions of the housing 20. For instance, and as shown in FIG. 5, the floor 24 is at times beneficially oriented perpendicular to an underlying substantially horizontal support surface. While the housing 20 is shown in this preferred embodiment having the exemplary shape, the housing 20 could have a variety of different shapes and still provide the basic function of this invention.

An interior of the housing 20 is provided inboard of the side walls 22 and above the floor 24. This interior is generally divided into the lower chamber 60 and the upper chamber 50 with a divider 40 between the lower chamber 60 and upper chamber 50. The divider 40 is preferably a separate piece from the housing 20 which is bonded or otherwise attached to the housing 20 after initial manufacture of the housing 20 to substantially separate the upper chamber 50 from the lower chamber 60. Note that the divider 40 does not entirely separate the upper chamber 50 from the lower chamber 60, but allows for a spillway 48 to provide communication between the upper chamber 50 and lower chamber 60 about a lip 46 of the divider 40.

With particular reference to FIGS. 2 and 9, details of the lower chamber 60 are described, according to this most preferred embodiment. In this embodiment depicted, the lower chamber 60 does not extend all the way to the side walls 22, but only takes up a portion of the space within the side walls 22 of the housing 20. This lower chamber 60 in this embodiment is shown with an elongate form and does extend substantially out to one of the side walls 22 on a portion of the lower chamber 60. The lower chamber 60 has a peripheral wall 62 which extends down to the floor 24 so that the peripheral wall 62 generally defines sides of the lower chamber 60, rather than the side walls 22. This configuration is particularly desirable when a high density phase H of the original mixed density sample O makes up a relatively small percentage of the original sample O.

While the lower chamber 60 is shown in this embodiment with an elongate form, the general benefit of accommodating a high density phase H which is a small percentage of the overall original sample O (e.g. less than ten to twenty percent) can still be achieved. In particular, a greater vertical spacing away from the floor 24 can be achieved if the lower chamber 60 has a smaller cross-sectional area than if it extends all the way to the side walls 22. This greater vertical height of the high density phase H makes the high density phase H easier to see and conveniently collect from other portions of the original sample O. By forming the lower chamber 60 being elongate and extending to the side walls 22 at one portion thereof, the lower chamber 60 is placed into fluid communication with the spillway 48 and minimizes potential for remixing after centrifugation and for full collection of the high density phase H away from other portions of the original sample O, such as a low density phase L (see FIG. 5). Addition of a medium density phase fluid is another way to gain further spacing of the high density phase H from the low density phase L.

The divider 40 has a peripheral edge 42 which is sized and shaped to be aligned with an upper portion of the peripheral wall 62 of the lower chamber 60. The divider 40 can thus be bonded or otherwise coupled to the housing 20 at the floor 24 and overlying the lower chamber 60, to divide the lower chamber 60 from the upper chamber 50 (see FIG. 9). This peripheral edge 42 does not entirely match the upper edge of the peripheral wall 62, in that the divider 40 has a lip 46 at one end thereof which stops short of the peripheral wall 62 adjacent this lip 46, so that the spillway 48 is provided around the divider 40 and joining the upper chamber 50 to the lower chamber 60. Also, a throughbore 44 is provided through the divider 40, preferably near a center of the overall housing 20. The extension tube 65 is coupled to this throughbore 44 and allows for removal of high density phase H fluid from the vessel 10 after centrifugation.

With particular reference to FIGS. 1, 2, 7 and 8, particular details of the cover 30 are described, according to this exemplary embodiment. The cover 30 in this embodiment is a generally planar and circular rigid structure having a substantially circular edge 32 with a diameter similar to that of the rim 23 of the housing 20. A tab 33 extends down from the edge 32 and preferably slightly inboard of the edge 32, such that the tab 33 can fit inboard of the rim 23 of the housing 20 with the edge 32 abutting the rim 23 of the housing 20 for a snug fit of the cover 30 upon the rim 23 of the housing 20. In this way, the cover 30 substantially encloses an interior of the housing 20 from an exterior environment.

The cover 30 preferably provides input and output access points into the housing 20. However, in alternative embodiments these access points could be provided through portions of the housing 20 rather than through the cover 30. Varying numbers of single purpose or dual use parts could alternatively be utilized.

Most preferably, a pair of ports are provided adjacent each other and near the edge 32, and preferably at a location substantially overlying the spillway 48. These two ports include an input port 35 and a vacuum port 34. In one embodiment the vacuum port is connected to a source of vacuum and the input port 35 is coupled to a source of an original sample O. The vacuum source provides motive force to draw the original sample S into the vessel 10. As depicted in FIG. 3, a vacuum tube V is coupled to the vacuum port 34 and an aspiration tube P is coupled to the input port 35, such that lipoaspirate (or other sample material) can be directly placed into the vessel 10.

The cover 30 also preferably includes a lower extraction port 36 near a center of the cover 30 and an upper extraction port 37 near the edge 32 and opposite the ports 34, 35. These extraction ports 36, 37 preferably include caps thereon and have a luer lock fitting or other fitting which conveniently allows for syringes or similar connectors to be coupled to these ports 36, 37. The lower extraction port 36 is coupled to the extraction tube 65 so that removal of the high density phase H can occur through the extraction tube 65 and then through the lower extraction port 36.

As depicted in FIG. 5, this extraction can occur by having a syringe Y coupled to the lower extraction port 36, and then removal of the high density phase H along arrow E. The upper extraction port 37 can be utilized for removing the low density phase L or portions of the mid density phase M, such as when the centrifuge vessel 10 is laying on its side (FIG. 5).

Feet 38 are preferably provided on either side of the upper extraction port 37. These feet 38 allow for orientation of the centrifuge vessel 10 properly to provide the upper extraction port 37 at a lowest possible position. The feet 38 also tend to keep the vessel 10 stable when in this orientation laying on its side. The cover 20 is preferably bonded to the housing 20 so that it cannot be moved. Alternatively, the cover 30 can be removably attachable to the housing 20, such as to facilitate sterilization of the centrifuge vessel 10 or as an alternative method for inputting an original sample O into the vessel 10, rather than inputting along arrow I (FIG. 3). In contrast to the extraction ports 36, 37, the ports 34, 35 are preferably merely nipples to which surgical tubing or other similar tubing can overlie. During centrifugation the extraction ports 36, 37 would typically be closed with caps. Caps could also be provided over the ports 34, 35 or they could be left open to allow for air exchange into and out of the housing 20 of the vessel 10.

With particular reference to FIGS. 3-6, basic details of the use and operation of the centrifuge vessel 10 are described, according to an exemplary embodiment. Initially, an original mixed density sample O is inputted into the centrifuge vessel 10 (FIG. 3). In one embodiment this inputting of the original sample O occurs through an aspiration tube P by suction provided from a source of vacuum coupled to the vessel 10 through a vacuum tube V, to cause flow of the original sample O into the vessel 10 along arrow I (FIG. 3). Once the sample O has been placed within the vessel 10, the vessel 10 is placed within a centrifuge C. While FIG. 4 depicts a centrifuge which supports the centrifuge vessel 10 laying on its side, most preferably the centrifuge C is a bucket type centrifuge which allows for pivoting of the centrifuge vessel 10 as its rotates. Thus, FIG. 4 generally depicts the orientation that the centrifuge vessel 10 would have after such pivoting and during centrifugation. While the angle of the centrifuge vessel 10 will not fully reach an orientation on its side, it will approach such an orientation. Most preferably, in this embodiment the divider 40 has an angular orientation of approximately 10° away from vertical, as depicted in FIG. 4. If the centrifuge vessel 10 does not go entirely to the orientation depicted in FIG. 4, this divider 40 can have its orientation modified so that the desired angular orientation of the divider 10 can be provided regardless of the type of centrifuge C utilized.

In this centrifuge C, the centrifuge vessel 10 rotates (about arrow B of FIG. 4) with a center of rotation aligned with a spin axis A of the centrifuge C. High gee forces G are exerted on the fluids within the centrifuge vessel 10. This causes the differing density phases within the original sample O (FIG. 3) to be stratified into separate layers (FIG. 4) such as including a high density phase H, medium density phase M and low density phase L. In one embodiment only two different density phases exist. In one embodiment a medium density fluid is added to enhance a separation between two or more phases of different density within the original sample O.

After such centrifugation, the three density phase fluid in this example is stratified as that depicted in FIG. 4. The high density phase H is entirely within the lower chamber 60. The low density phase L is entirely within the upper chamber 50. The centrifuge vessel 10 can then be removed from the centrifuge C and placed on its side (FIG. 5). Note that the high density phase H remains within the lower chamber 60 because the spillway 48 joining the chambers 50, 60 together is now at a highest portion of the vessel 10.

One can then readily extract the high density phase H, such as through the extraction tube 65 by coupling of a syringe Y and removal of the fluid H along arrow E. When the original sample O is a lipoaspirate sample, this high density phase H is the cell pellet. In this instance the mid density phase M is an aqueous phase of the lipoaspirate and it is acceptable to have some of this aqueous phase harvested along with the high density phase H. Other portions of this medium density phase M might remain with the low density phase L.

If desired, more of this aqueous mid density phase M can be removed through the upper extraction port 37. However, most preferably extraction of the low density phase L, such as adipose tissue and oils can occur without collection of an appreciable portion of the aqueous phase utilized in the following method. First, the centrifuge vessel 10 is returned to an upright orientation (by rotation along arrow R of FIG. 6). Remaining aqueous phase or other medium density phase M fluid is caused to flow into the lower chamber 60. The low density phase L in the form of adipose tissue and oil will tend to block the spillway 48 to facilitate full separation of the medium density phase M after collection within the lower chamber 60 and reorientation of the centrifuge vessel 10 back onto its side (by rotation of the vessel 10 about arrow R'). A surface of the mid density phase M will shift from surface T to surface T' after such reorientation. Extraction can then occur along arrow E' for removal of the medium density phase M fluid such as the aqueous phase of a lipoaspirate original sample O. The low density phase L will have its surface S reoriented to become the surface S' (FIG. 6) and can then be extracted through the upper extraction port 37 along arrow F. Substantially pure adipose tissue and oil can thus be readily collected.

Figure 14:
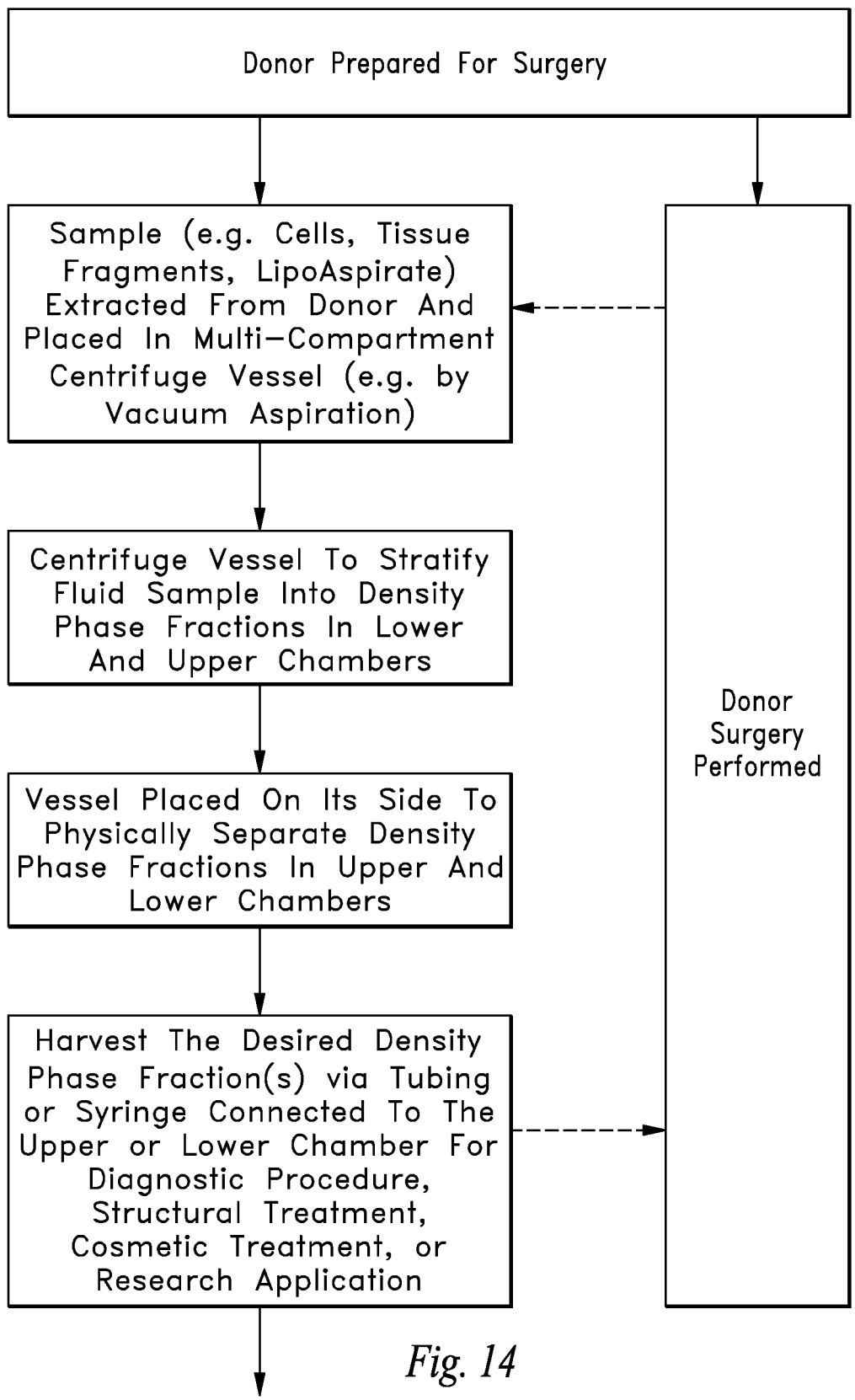
FIG. 14 is a flow chart identifying steps in the use of the centrifuge vessel of this invention and centrifugation methods of this invention in one particular embodiment for separation of a donor sample during a surgical procedure.

The centrifuge vessel 10, while conceivable cleanable for reuse, typically in a biological setting will be manufactured to be a single use disposable device. In this manner, the vessel 10 is particularly useful in autologous cell therapy procedures. The speed and simplicity of separation and extraction of the various different phases H, M, L of the original sample O facilitate autologous donor tissue processing during surgery, such that autologous sample constituents can be harvested and used at the end of the surgery or during the surgery, or otherwise utilized for research, or can be stored for later use by the donor patient. A general flow diagram for this use, such as exemplified in the processing of lipoaspirate, is depicted in FIG. 14.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A method for separation of a heterogeneous fluid sample having constituents of differing density, the method including the steps of:

identifying a centrifuge vessel with a housing including a floor and a side wall extending up from the floor; at least two chambers including a lower chamber and an upper chamber, the lower chamber closer to the floor than the upper chamber; a divider wall interposed between the upper chamber and the lower chamber; a spillway around the divider wall, the spillway joining the upper chamber to the lower chamber; and an outlet comprising a conduit that extends from the lower chamber through the divider wall and out of the housing, such that a constituent of the heterogeneous fluid sample within the lower chamber can be removed from the lower chamber;

inputting the heterogeneous fluid sample with constituents of differing densities into the vessel of said identifying step;

centrifuging the vessel with gee forces oriented substantially toward the floor until the heterogeneous fluid sample is separated into at least two differing density fluids including a higher density phase and a lower density phase; and extracting the higher density phase from the lower chamber through the outlet.

2. The method of claim 1 including the further step of rotating the centrifuge vessel onto the side wall with the floor non-parallel with a horizontal surface and with a lip of the divider wall at the spillway defining a highest portion of the divider wall before said extracting step.

3. The method of claim 2 wherein said inputting step includes the heterogeneous fluid having at least three separate fluids including a medium density fluid; and the further step of removing said medium density fluid by rotating the housing back to vertical with the floor at a lowermost portion of the housing before extracting the medium density phase fluid through said outlet.

4. The method of claim 3 including the further step of removing the lower density fluid by rotating the vessel back to horizontal with the floor non-parallel with a horizontal surface with extraction through a second outlet coupled to the upper chamber of the vessel.

5. The method of claim 1 wherein said identifying step includes the housing having an inlet passing thereinto, the inlet used in said inputting step to allow the heterogeneous fluid sample to be passed into the housing of the vessel during said inputting step.

6. The method of claim 1 wherein said identifying step includes a cover enclosing the housing, the cover on a side of the housing opposite the floor; and
wherein the conduit extends from the lower chamber and passes out of the housing through the cover.

7. The method of claim 1 wherein said identifying step includes a pair of feet extending from the side wall and perpendicular to the floor, the feet supporting the housing during said extracting step when resting on the side wall upon a substantially horizontal surface with the floor extending substantially perpendicular to the surface.

* * * * *